US011399762B1

(12) United States Patent
Feuer

(10) Patent No.: US 11,399,762 B1
(45) Date of Patent: Aug. 2, 2022

(54) MODULAR ELECTROENCEPHALOGRAPH (EEG) SYSTEM

(71) Applicant: Starcat LLC, Seattle, WA (US)

(72) Inventor: Henry Adam Feuer, Seattle, WA (US)

(73) Assignee: STARCAT LLC, Seattle, WA (US)

( * ) Notice: Subject to any disclaimer, the term of this patent is extended or adjusted under 35 U.S.C. 154(b) by 0 days.

(21) Appl. No.: 17/394,637

(22) Filed: Aug. 5, 2021

(51) Int. Cl.
*A61B 5/30* (2021.01)
*A61B 5/31* (2021.01)
*A61B 5/00* (2006.01)
*A61B 5/273* (2021.01)
*A61B 5/369* (2021.01)
(Continued)

(52) U.S. Cl.
CPC .............. *A61B 5/31* (2021.01); *A61B 5/0006* (2013.01); *A61B 5/0022* (2013.01); *A61B 5/273* (2021.01); *A61B 5/30* (2021.01); *A61B 5/304* (2021.01); *A61B 5/308* (2021.01); *A61B 5/313* (2021.01); *A61B 5/318* (2021.01); *A61B 5/369* (2021.01); *A61B 5/389* (2021.01); *A61B 5/6898* (2013.01); *A61B 5/7225* (2013.01); *A61B 2560/0214* (2013.01); *A61B 2560/0443* (2013.01); *A61B 2562/223* (2013.01); *A61B 2562/225* (2013.01)

(58) Field of Classification Search
CPC .... A61B 5/30; A61B 5/304; A61B 5/307–315
See application file for complete search history.

(56) References Cited

U.S. PATENT DOCUMENTS 5,381,804 A  1/1995 Shambroom
7,881,778 B2  2/2011 Rantala
(Continued)

FOREIGN PATENT DOCUMENTS

CN  108433729 A  8/2018
JP  5351312 B2  11/2013
RU  2552876 C2  6/2015

OTHER PUBLICATIONS

Jain, Ankit. May 2012. Low Cost Instrumentation and Interface for Neural Recordings (Master's thesis, Pennsylvania State University). Retrieved from https://etda.libraries.psu.edu/catalog/13321 (Year: 2012).*

(Continued)

*Primary Examiner* — Meredith Weare
(74) *Attorney, Agent, or Firm* — Flener IP & Business Law; Zareefa B. Flener; Ayhan E. Mertogul

(57) ABSTRACT

A modular electroencephalograph (EEG) system comprises a carrier board comprising one or more electrode connectors, one or more power supplies, and one or more analog-to-digital converter (ADC) modules. Each of the ADC modules comprises multiple input channels, input signal routing, at least one instrumentation power supply, configuration switches for the at least one instrumentation power supply and the input signal routing, an ADC, a programmable gain amplifier, and an ADC communications bus. Each of the one or more ADC modules electrically connects to one of the one or more electrode connectors and one of the one or more power supplies of the carrier board. An embedded computer is configured to run a real time operating system (RTOS), wherein each ADC communications bus of the one or more ADC modules is electrically connected to the embedded computer via a serial interface.

23 Claims, 7 Drawing Sheets

(51) Int. Cl.
   *A61B 5/389* (2021.01)
   *A61B 5/318* (2021.01)
   *A61B 5/308* (2021.01)
   *A61B 5/313* (2021.01)
   *A61B 5/304* (2021.01)

(56) References Cited

U.S. PATENT DOCUMENTS

| | | | |
|---|---|---|---|
| 7,896,807 B2 | 3/2011 | Clancy et al. |
| 8,068,905 B2 | 11/2011 | Freeman et al. |
| 8,348,841 B2 | 1/2013 | Varadan |
| 8,755,877 B2 | 6/2014 | Zoica |
| 8,764,651 B2 | 7/2014 | Tran |
| 8,805,527 B2 | 8/2014 | Mumford |
| 9,155,487 B2 | 10/2015 | Linderman |
| 9,393,418 B2 | 6/2016 | Giuffrida |
| 9,542,531 B2 | 1/2017 | Chmiel et al. |
| 9,610,016 B2 | 4/2017 | Shusterman |
| 9,882,428 B2 | 1/2018 | Calhoun et al. |
| 10,383,571 B1 | 8/2019 | Pulliam |
| 2010/0036211 A1 | 2/2010 | La Rue et al. |
| 2011/0319777 A1 | 12/2011 | Mehrotra et al. |
| 2013/0338449 A1 | 12/2013 | Warwick et al. |
| 2017/0112392 A1 | 4/2017 | Wu |
| 2018/0239430 A1 | 8/2018 | Tadi et al. |
| 2019/0090747 A1 | 3/2019 | Evans et al. |
| 2019/0104992 A1 | 4/2019 | Magar et al. |

OTHER PUBLICATIONS

Notification of Transmittal of the International Search Report and the Written Opinion of the International Searching Authority or the Declaration, PCT/US21/44620, dated Nov. 26, 2021.

* cited by examiner

MODULAR ELECTROENCEPHALOGRAPH (EEG) SYSTEM

FIELD OF THE INVENTION

The present invention relates to modular electroencephalograph (EEG) system. More specifically, the present invention relates to a modular EEG system including a plurality of separate identical analog to digital converter (ADC) modules each connected with an embedded computer via a direct serial connection.

BACKGROUND OF THE INVENTION

Portable electroencephalographs (EEGs) are known in the art. However, existing devices utilize electronic modules that communicate with a central processor or CPU via a single bus, where each electronic module includes at least an ADC and a CPU. Communication of multiple such modules over the single bus can limit data transfer speed from the multiple individual modules. Further, the inclusion of a CPU on each electronic module adds to the cost of production.

A need therefore exists for a modular EEG system that includes a plurality of ADC modules that do not include individual CPUs and where the ADC modules each communicate with an embedded central processor or CPU via direct serial connections. It would be advantageous if the embedded CPU ran a real time operating system (RTOS) and if the EEG system further included a communications computer that communicates with the RTOS CPU. It would be further advantageous if the communications computer could communicate with external devices wirelessly.

SUMMARY OF THE INVENTION

In one aspect of the invention, a modular electroencephalograph (EEG) system comprises a carrier board comprising one or more electrode connectors, one or more power supplies, and one or more analog-to-digital converter (ADC) modules. Each of the ADC modules comprises multiple input channels, input signal routing, at least one instrumentation power supply, configuration switches for the at least one instrumentation power supply and the input signal routing, an ADC, a programmable gain amplifier, and an ADC communications bus. Each of the one or more ADC modules electrically connects to one of the one or more electrode connectors and one of the one or more power supplies of the carrier board. An embedded computer is configured to run a real time operating system (RTOS), wherein each ADC communications bus of the one or more ADC modules is electrically connected to the embedded computer via a serial interface.

In another aspect of the invention, modular electroencephalograph (EEG) system comprises a carrier board comprising one or more electrode connectors, one or more power supplies, and one or more analog-to-digital converter (ADC) modules. Each of the ADC modules comprises multiple input channels, input signal routing, at least one instrumentation power supply, configuration switches for the at least one instrumentation power supply and the input signal routing, an ADC, a programmable gain amplifier, and an ADC communications bus. Each of the one or more ADC modules electrically connects to one of the one or more electrode connectors and one of the one or more power supplies of the carrier board. The modular electroencephalograph (EEG) system further comprises a field-programmable gate array (FPGA), wherein each ADC communications bus of the one or more ADC modules is electrically connected to the FPGA via a serial interface, and an embedded computer electrically connected to the FPGA via a high-speed interconnect bus.

BRIEF DESCRIPTION OF THE DRAWINGS

Other aspects and advantages of the present invention will become apparent upon consideration of the following detailed description, wherein similar structures have similar reference numerals.

DETAILED DESCRIPTION

Figure 1:
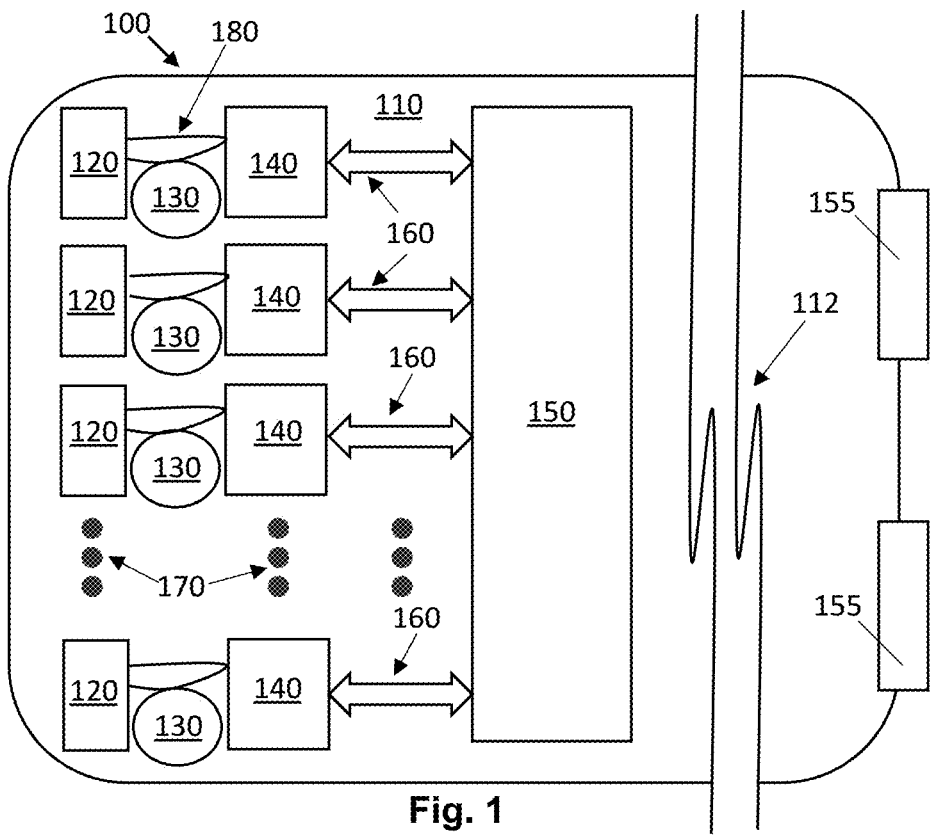
FIG. 1 is a schematic view of an exemplary embodiment of a modular EEG system.

The following detailed embodiments presented herein are for illustrative purposes. That is, these detailed embodiments are intended to be exemplary of the present invention for the purposes of providing and aiding a person skilled in the pertinent art to readily understand how to make and use of the present invention. In the descriptions that follow identical reference numerals used to describe components of different disclosed embodiments refer to identical components that may be part of the different disclosed embodiments.

FIGS. 1-11 as described hereinbelow illustrate embodiments and aspects of a modular internet connectable EEG system suitable for collecting and digitizing electrical signals from humans, animals, and other biological sources. The illustrated embodiments of the modular EEG system can also be used as electrocardiographs (EKG) and electromyographs (EMG).

Referring to FIG. 1, an embodiment of a modular EEG system 100 is presented in a schematic block diagram format illustrating an exemplary configuration of some components of the modular EEG system 100 arranged on a portion of a carrier board 110. As indicated by the break lines 112, the carrier board 110 can have a larger extent than shown to accommodate other components as will be more fully described hereinbelow. The carrier board 110, for example, a printed circuit board or other board including connections for electrical components mounted thereon, supports one or more electrode connectors 120, one or more power supplies 130, and one or more separate identical ADC modules 140. Each of the one or more ADC modules 140 is connected to a computer 150 embedded on the carrier board 110. The embedded computer 150 is configured to run a real time operating system (RTOS). For example, in an embodiment the RTOS is NuttX, whereas in another embodiment the RTOS is Linux. In other embodiments the RTOS can be any suitable RTOS as is known in the art.

Each ADC module 140 has a communications bus 152 (see FIG. 4) that is electrically connected to the embedded computer 150 via a serial interface, for example without limitation, a Serial Peripheral Interface (SPI), shown as the double arrow 160. In an embodiment the carrier board 110 further comprises and/or accommodates one or more battery connectors 155. The carrier board 110 in an embodiment further includes an input port (not shown) for a charger for charging batteries (not shown) onboard the carrier board 110. The input port and charger can be any sort of charger, for example, a USB, a USB-C, a lightning port, or any sort of charging port as is known in the art that can charge rechargeable batteries electrically connected with the carrier board 110.

Figure 11:
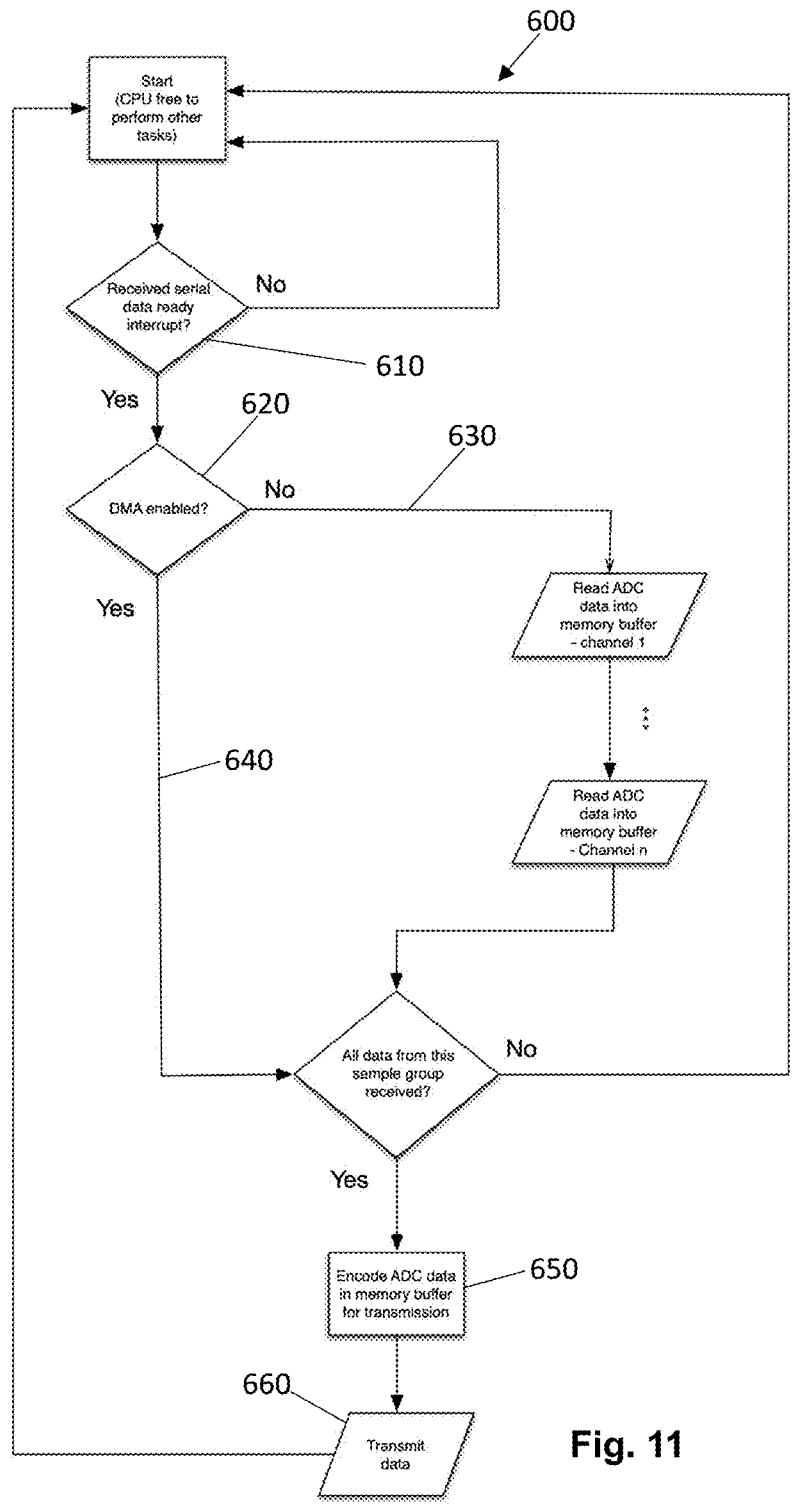
FIG. 11 is a flowchart representative of exemplary steps taken by driver software configured to run on the RTOS of the embedded computer to transfer data from one or more ADC modules optionally using direct memory access (DMA), according to an embodiment of the invention.

In an embodiment the RTOS of the embedded computer 150 communicates via internet TCP/IP protocols and is connected to a network. In an embodiment the embedded computer is configured to run a special purpose software driver configured to transfer data from the one or more ADC modules 140 to the embedded computer 150, optionally using direct memory access (DMA). Referring to FIG. 11, in an embodiment, at step 610, the special purpose software driver 600 receives interrupts from the serial interfaces 160 when data from an ADC 148 is ready. For each interrupt, the driver 600 checks which ADC 148 the data is from. Then at step 620 the driver 600 either reads the data into memory along path 630, or follows path 640 if the implementation is using DMA, and locates where the CPU's DMA engine has placed the data into memory without the action of the driver 600. (Direct Memory Access refers to a component of the CPU that can read data from peripherals like a serial interface, and place it into main memory quickly without using the CPU's computing power.) At step 650 the software driver 600 then encodes the data sample along with other data samples from the other ADC's 148 for a particular time period, and at step 660 transmits the data samples via a network interface to user device 250, or optionally to the communications computer 230 (see FIG. 5) and then to the user device 250.

The number of ADC modules 140 that can be accommodated by the carrier board 110 can vary with the size of the board as indicated symbolically by the three dashed dots 170 in FIG. 1. In an embodiment the carrier board 110 can accommodate two ADC modules 140. In other embodiments the carrier board 110 can accommodate 3, 4, 5, 6, 7, 8, 9, 10, or more ADC modules. In an embodiment each of the ADC modules 140 comprises a plurality of input channels, for example without limitation, eight input channels. In other embodiments each of the ADC modules 140 comprises a plurality of input channels other than eight channels, for example, any number of channels from 1 to 256, or more.

Figure 2:
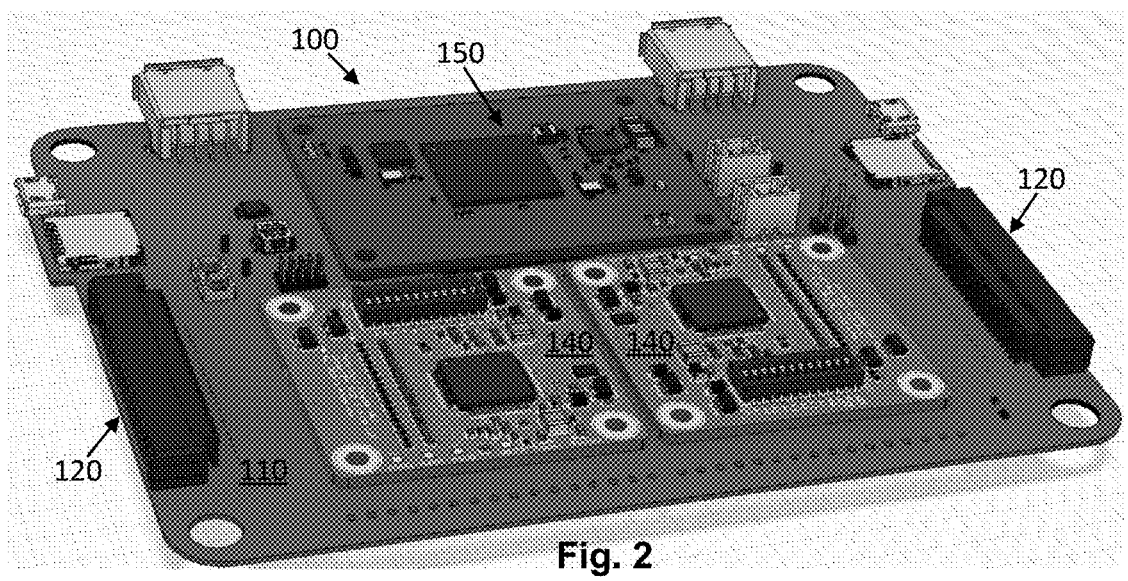
FIG. 2 an image of a carrier board according to an embodiment of the invention.

Still referring to FIG. 1, each of the one or more ADC modules 140 electrically connects to one of the one or more electrode connectors 120 and also to one of the one or more power supplies 130 of the carrier board, for example via connections 180. The electrode connectors 120 comprise structures for connecting to electrodes that are applied to a subject's body for measurement of electrical impulses, for example, through the skin of the subject. The electrode connectors 120 in an embodiment are posts that snap into loops on the end of wires connected to electrodes. In other embodiments the electrode connectors 120 are loops that accept and engage with posts on the end of wires connected to electrodes. In other embodiments the electrode connectors 120 are other connectors as are known in the art including clips, snap buttons, and the like. FIG. 2 shows an image of a carrier board 110 having a computer 150 and two ADC modules 140 connected thereon, where each of the ADC modules is connected with an adjacently disposed electrode connector 120.

Figure 3:
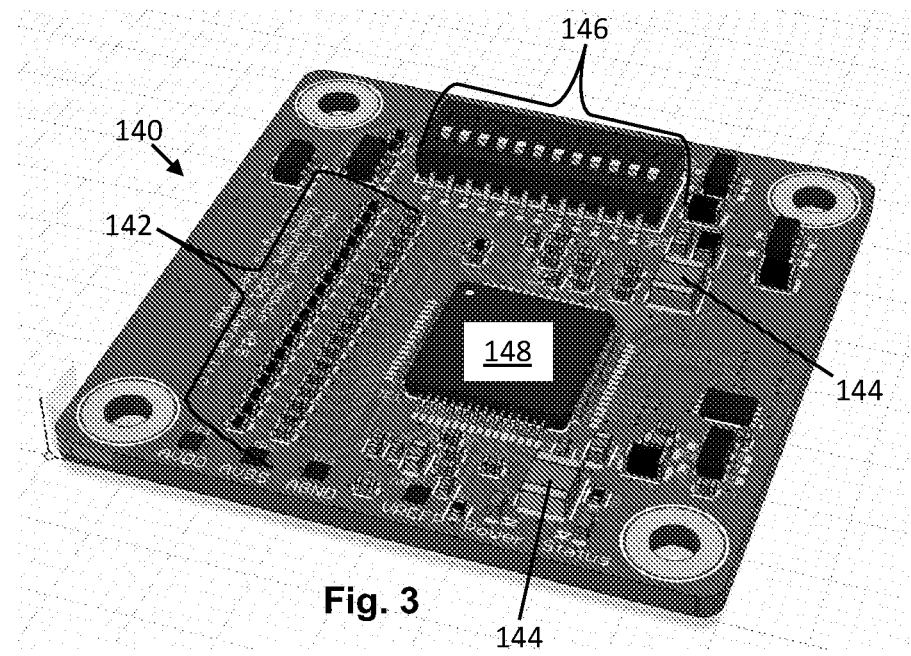
FIG. 3 is an image of a top side of an ADC module according to an embodiment of the invention.
Figure 4:
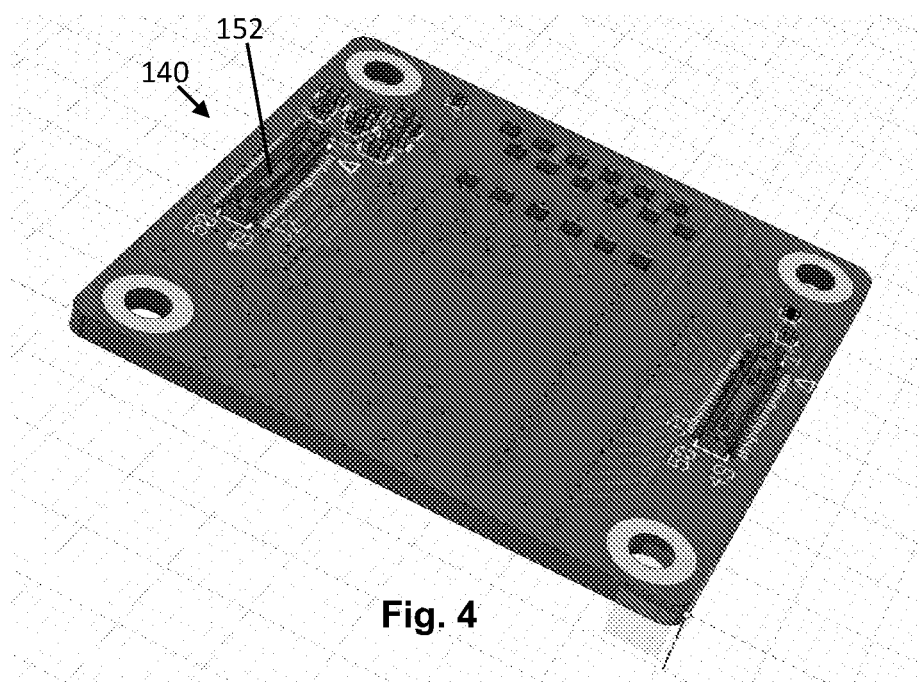
FIG. 4 is an image of a bottom side of an ADC module according to an embodiment of the invention.

Referring to FIGS. 3 and 4, which show the top and bottom sides of an exemplary ADC module 140, respectively, each of the ADC modules 140 further comprises multiple input channels, for example without limitation eight input channels, wherein each input channel is single ended or differential, and switchable circuitry 142 configured for input signal routing. Each ADC module 140 further comprises at least one and preferably two instrumentation power supplies 144 (described further hereinbelow), and configuration switches 146 for configuring the at least one instrumentation power supply 144 and the switchable signal routing circuitry 142. Each ADC module 140 further includes an ADC 148, a programmable gain amplifier (built into the ADC 148), and an ADC communications bus 152, for example without limitation, a serial interface (such as Serial Peripheral Interface or SPI). The disclosed structure of the ADC modules 140 allows for each ADC module 140 to be manufactured separately, with high quality, and economically, with different numbers of ADC modules 140 attached to different carrier boards 110, resulting in varying total numbers of input channels for the modular EEG system 100 as a whole, for example without limitation, in an embodiment there are eight channels per ADC module 140, so different numbers of ADC modules 140 lead to 8, 16, 24, 32 and so forth up to 64 or even up to 256 or more channels.

Figure 10:
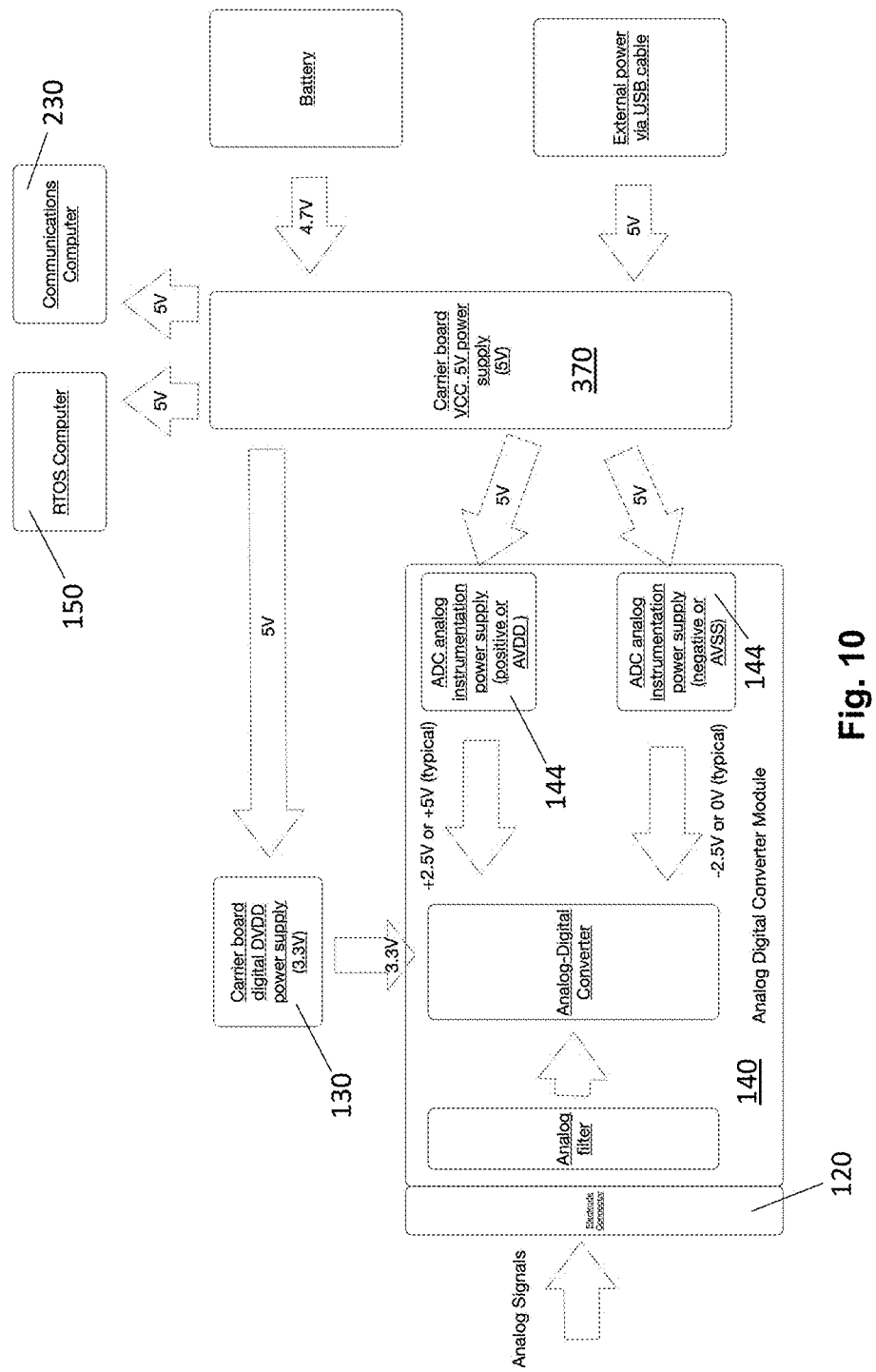
FIG. 10 is a schematic view of the power flow from the carrier board to an exemplary ADC module according to an embodiment of the invention.

Referring briefly to FIG. 10, the power flow from the carrier board 110 to an exemplary ADC module 140 is illustrated. Each ADC module 140 is electrically connected to one of the one or more power supplies 130 disposed on the carrier board 110. Further, each ADC module 140 preferably includes two instrumentation power supplies 144, wherein one is an AVDD or positive analog instrumentation power supply and the other is an AVSS or negative analog instrumentation power supply. The instrumentation power supplies 144 are specially designed to have very low noise and high precision and stability because the ADC 148 needs to have very clean power for its analog supplies. It is important for the instrumentation power supplies 144 be located on the ADC module 140 and near to the ADC 148. In an embodiment the carrier board 110 further includes its own power supply labeled as reference numeral 370, which provides power to onboard components other than the ADC modules 140, and which is powered either by a battery or an external source of power as is known in the art.

Figure 5:
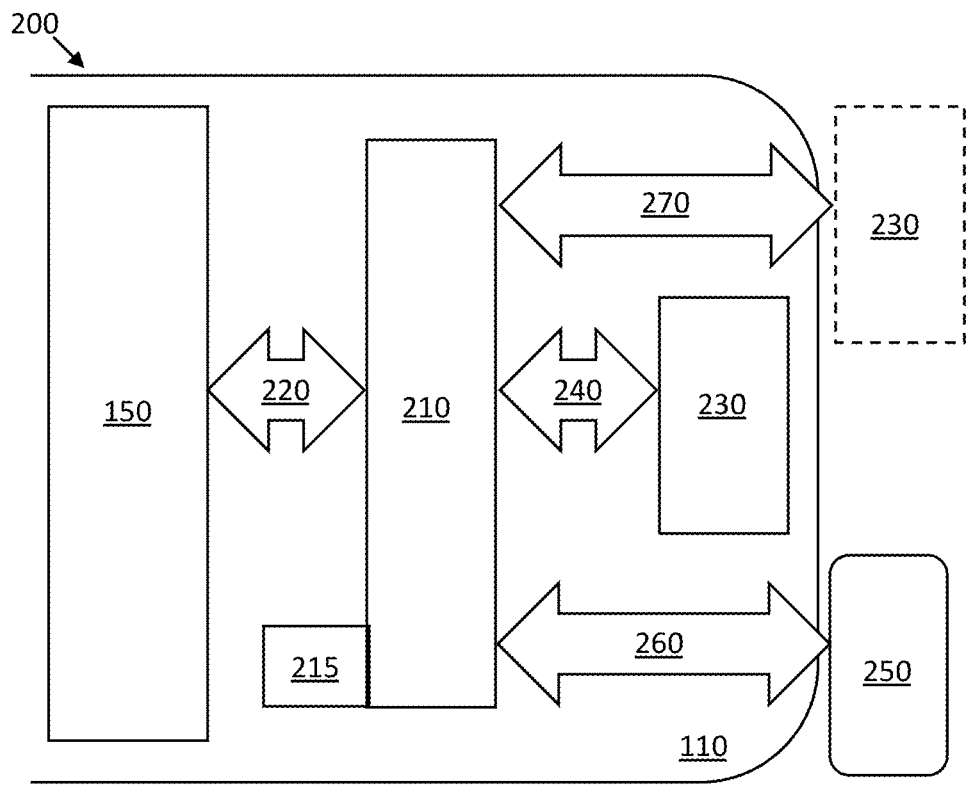
FIG. 5 is a schematic view of a portion of another exemplary embodiment of a modular EEG system.

Referring to FIG. 5, which shows a portion of the carrier board 110 to the right of the computer 150, in an embodiment the modular EEG system 200 further includes an optional universal serial bus (USB) multiplexer/demultiplexer 210 electrically connected to the embedded computer 150, via a connection 220, for example without limitation, via a USB network connection 220. In an embodiment a communications computer 230 is also disposed on the carrier board 110 and connected with the optional USB multiplexer/demultiplexer 210 via another connection 240, for example without limitation, via a USB connection 240.

A user device 250, for example without limitation, a laptop, smartphone, desktop, or other computing device is also connected with the optional USB multiplexer/demultiplexer 210 via a further connection 260, for example without limitation, via a USB connection or Ethernet over optical fiber connection 260. In other embodiments the communications computer 230 is not disposed on the carrier board 110 (as indicated by the dashed lines representing the communications computer 230) but is nevertheless connected either with the optional USB multiplexer/demultiplexer 210 via another connection 270, for example without limitation, via a USB connection; or with an Ethernet over optical fiber connection 270.

Still referring to FIG. 5, the optional USB multiplexer/demultiplexer 210 is configured to switch electrical connections to the RTOS of the embedded computer 150 between the communications computer 230 and the user device 250. The ability to switch electrical connections between devices enables one printed circuit board to be made that can be used wirelessly with a built in communications computer 230, or with a user device 250, resulting in reduced cost and risk. The optional USB Multiplexer/Demultiplexer 210 can be controlled by software running on the embedded computer 150 or via one or more manual control switches 215 as illustrated in FIG. 5. In some embodiments, the optional USB multiplexer/demultiplexer 210 is omitted, and the communications computer 230 or the user device 250 is connected directly with the embedded computer 150 for example, via the connection 240, 270, or via the connection 260, respectively.

Figure 6:
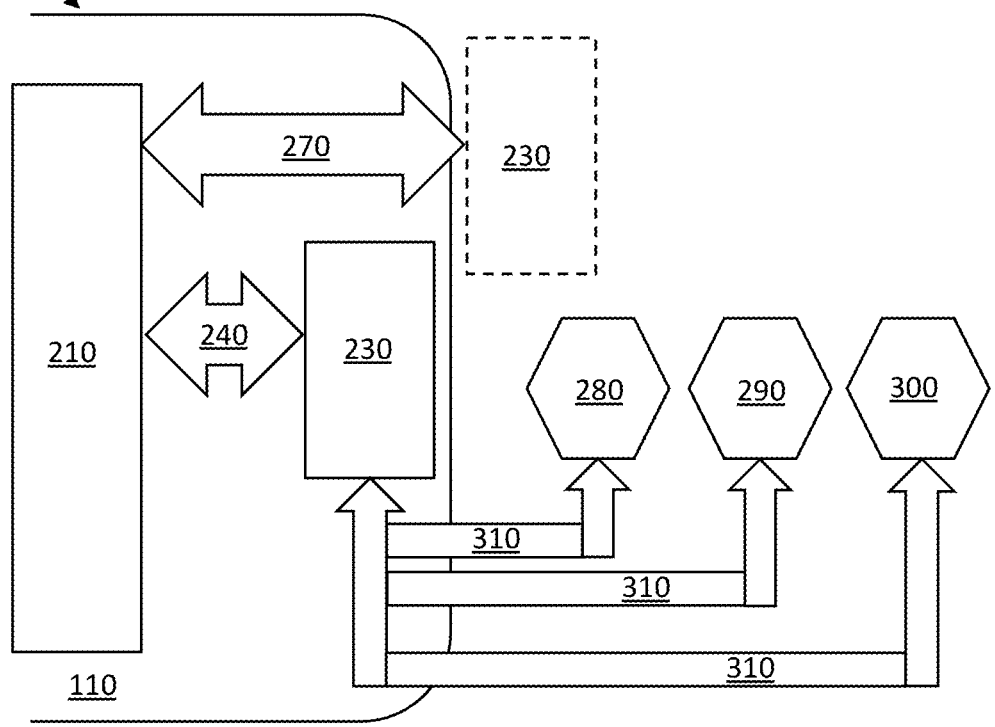
FIG. 6 is a schematic view of a portion of a further exemplary embodiment of a modular EEG system.

FIG. 6 shows an embodiment the modular EEG system 300 that is similar to the modular EEG system 200 shown in FIG. 5 except for the following differences. In this embodiment, one or more wireless communications adapters illustrated, for example, as reference numerals 280, 290, and 300 are each electrically connected to the communications computer 230 via a serial bus 310. In an embodiment the wireless communications adapter 280 is a Bluetooth adapter, in another embodiment the wireless communications adapter 290 is a WiFi adapter, and in another embodiment the wireless communications adapter 300 is another sort of wireless communications adapter as is known in the art. In an embodiment the serial bus 310 is a USB and in another embodiment the serial bus 310 is SPI. In other embodiments the serial bus 310 is another sort of serial bus as is known in the art.

The combination of the embedded computer 150 with many serial interfaces 160, connected to the communications computer 230 by internet protocols running over USB enables high bandwidth communication, which in turn enables high sampling rates of high resolution data. For example, in an embodiment where the communications computer 230 communicates via a WiFi adapter 290 the modular EEG system 300 can digitize and transmit 64 channels of 24 bit ADC data at 16,384 samples per second if using a network over USB 2.0; or 256 channels of 24 bit ADC data at 16,384 samples per second if using a network over USB 3.0.

Figure 7:
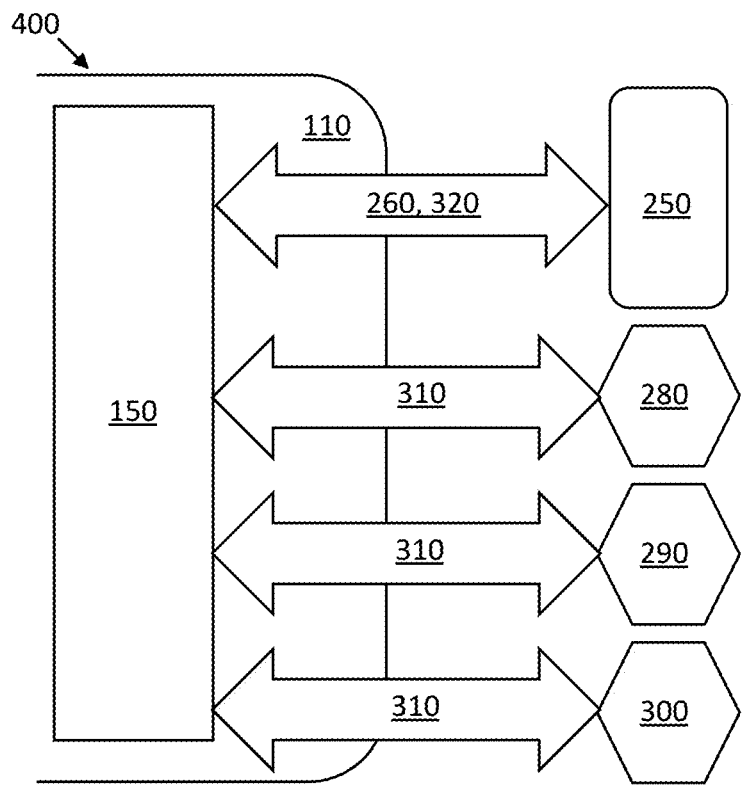
FIG. 7 is a schematic view of a portion of yet another exemplary embodiment of a modular EEG system.

Referring to FIG. 7, in an embodiment of the modular EEG system 400, the user device 250, for example, a laptop, smartphone, desktop, or other computing device is connected directly to the embedded computer 150 via a network connection 260, for example without limitation, via a USB connection 320. In another embodiment the one or more wireless communications adapters 280, 290, 300 are electrically connected to the embedded computer 150 via the serial bus 310.

Figure 8:
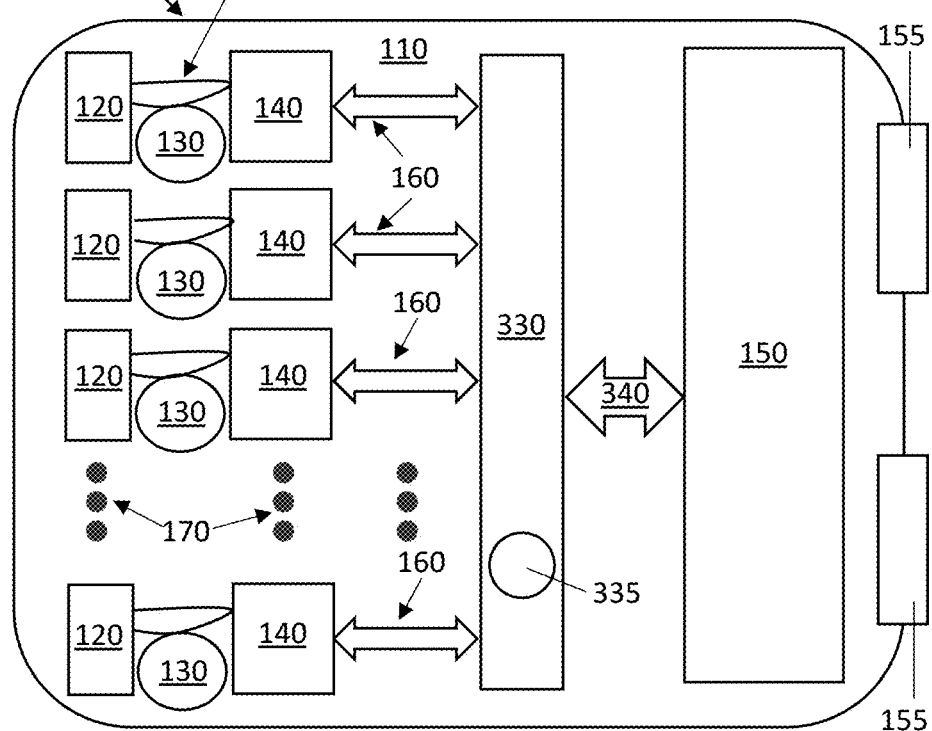
FIG. 8 is a schematic view of a still further embodiment of a modular EEG system.

Referring to FIG. 8, an embodiment of the modular EEG system 500 comprises the carrier board 110, which supports the one or more electrode connectors 120, the one or more power supplies 130, and the one or more ADC modules 140. In this embodiment each of the one or more ADC modules 140 has a communications bus 152 (see FIG. 4) that is connected to a field-programmable gate array (FPGA) 330, wherein each ADC communications bus 152 of the one or more ADC modules 140 is electrically connected to the FPGA 330 via a Serial Peripheral Interface (SPI) as shown as the double arrow 160.

In an embodiment, the FPGA 330 includes an optional functional unit 335, schematically shown on FIG. 8 as the circular element 335, that can timestamp outgoing ADC data from each ADC module 140. In an embodiment the embedded computer 150 electrically connects to the FPGA 330 via a high-speed interconnect bus 340, for example without limitation, an Advanced eXtensible Interface (AXI) bus. For example, in an embodiment, the FPGA 330 is configured as an array of serial interfaces (for example, SPI) 160, and including the optional functional unit 335 that can timestamp data, wherein the serial interfaces 160 connect to the one or more ADC modules 140. The optional functional unit 335 configured into the FPGA 330 enables accurate timestamping of each ADC sample received from the one or more ADC modules 140 via the serial interfaces 160.

The serial interfaces 160 can optionally be serviced by the embedded computer 150 directly enabling high data transfer rates and low CPU loads. A reason why the FPGA 330 is used is that there are currently no commercial, high-speed, high-density SPI communications adapter chips, so configuring the FPGA 330 with the above described functionality is practical, cost effective, and compact in terms of printed circuit board space.

The one or more ADC modules 140 and the interconnections therewith of the modular EEG system 500 are identical to those described hereinabove, for example, in regard to the modular EEG system 100 of FIG. 1. In an embodiment the carrier board 110 further comprises one or more battery connectors 155 as shown in FIG. 8.

Figure 9:
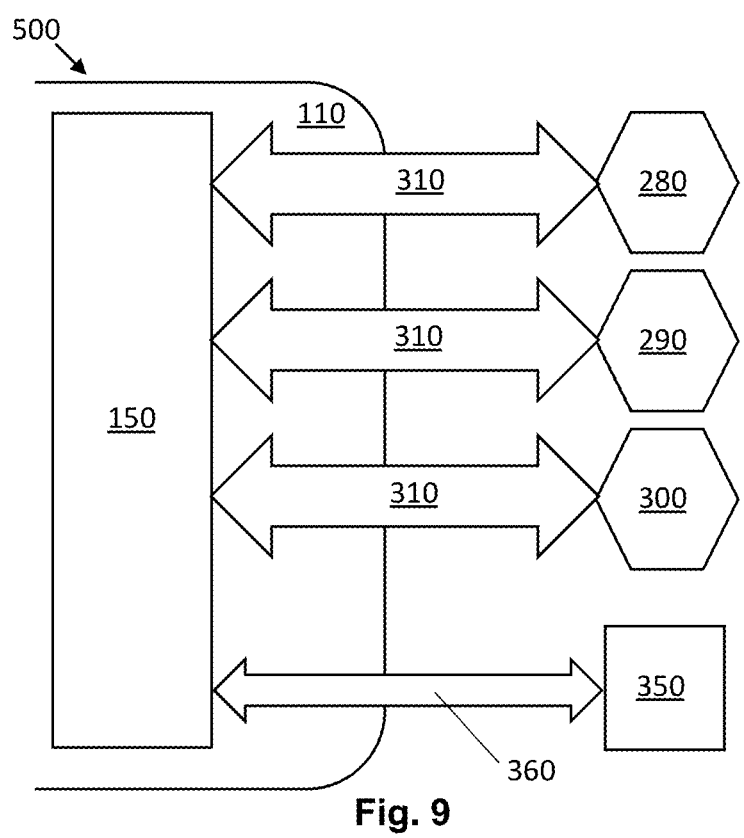
FIG. 9 is a schematic view of a portion of yet a further exemplary embodiment of a modular EEG system.

Referring to FIG. 9, the modular EEG system 500 in an embodiment further comprises one or more wireless communications adapters 280, 290, 300 each electrically connected to the embedded computer 150 via the serial bus 310. The modular EEG system 500 in an embodiment further includes a wired communications adapter 350 electrically connected to the embedded computer 150, optionally via an electrical isolation device 360. The wired communications adapter 350 in an embodiment is an ethernet adapter 350; however, in other embodiments the wired communications adapter 350 can be an Ethernet over optical fiber adapter, or any sort of wired communications as is known in the art.

Any of the modular EEG systems 100, 200, 300, 400, 500 disclosed hereinabove can be configured to operate as an electroencephalograph (EEG), an electrocardiograph (EKG), or an electromyograph (EMG). Those embodiments of the EEG modular systems 100, 200, 300, 400, 500 disclosed hereinabove that include a smartphone or laptop further can include a special-purpose application that would run on the smartphone or laptop, communicate with the embedded computer 150, and handle communication via WiFi, Bluetooth, Ethernet, Ethernet over optical fiber, or other wireless or network protocols.

INDUSTRIAL APPLICABILITY

A modular electroencephalograph (EEG) system comprises a plurality of separate identical analog to digital converter (ADC) modules each connected with an embedded computer via a direct serial connection. Each of the plurality of ADC modules does not include a CPU but rather each of the ADC modules communicates with an embedded central processor or CPU via direct serial connections. The modular EEG system can also be used as an electrocardiograph (EKG) and an electromyograph (EMG). The modular EEG can be manufactured in industry for use by health professionals, first responders, and other consumers.

Numerous modifications to the present invention will be apparent to those skilled in the art in view of the foregoing description. It is not desired to limit the invention to the exact construction and operation shown and described, and accordingly, all suitable modifications and equivalents may be resorted to, falling within the scope of the invention. Accordingly, this description is to be construed as illustrative only of the principles of the invention and is presented for the purpose of enabling those skilled in the art to make and use the invention and to teach the best mode of carrying out same. The exclusive rights to all modifications which come within the scope of the appended claims are reserved. All patents, patent publications and applications, and other references cited herein are incorporated by reference herein in their entirety.

What is claimed is:

1. A modular system for collecting and digitizing electrical signals, the system comprising:
    a carrier board comprising:
        one or more electrode connectors;
        one or more power supplies; and
        one or more analog-to-digital converter (ADC) modules, each ADC module comprising:
            multiple input channels;
            input signal routing circuitry;
            at least one instrumentation power supply;
            configuration switches for the at least one instrumentation power supply and the input signal routing;
            an ADC;
            a programmable gain amplifier; and
            an ADC communications bus; wherein
        each of the one or more ADC modules electrically connects to one of the one or more electrode connectors and one of the one or more power supplies of the carrier board; and
    an embedded computer configured to run a real time operating system (RTOS), wherein each ADC communications bus of the one or more ADC modules is directly electrically connected to the embedded computer via a separate serial interface.

2. The modular system of claim 1, wherein the serial interface is a Serial Peripheral Interface (SPI).

3. The modular system of claim 1, further comprising a communications computer electrically connected to the embedded computer via a network connection.

4. The modular system of claim 3, wherein the network connection between the embedded computer and the communications computer is via a universal serial bus (USB) connection.

5. The modular system of claim 3, further comprising one or more wireless communications adapters each electrically connected to the communications computer via a serial bus.

6. The modular system of claim 1, further comprising a user device electrically connected to the embedded computer via a network connection.

7. The modular system of claim 6, wherein the user device is a computer or a smartphone.

8. The modular system of claim 6, wherein the network connection between the embedded computer and the user device is via a universal serial bus (USB) connection.

9. The modular system of claim 6, wherein the network connection between the embedded computer and the user device is via an Ethernet over optical fiber connection.

10. The modular system of claim 1, further comprising:
    a universal serial bus (USB) multiplexer/demultiplexer electrically connected to the embedded computer;
    a communications computer; and
    a user device;
        wherein the communications computer and the user device are each electrically connected to the USB multiplexer/demultiplexer via a wired USB connection, and
        wherein the USB multiplexer/demultiplexer is configured to switch electrical connections to the embedded computer between the communications computer and the user device.

11. The modular system of claim 10, wherein the user device is electrically connected to the communications computer via a network connection, wherein the network connection is an Ethernet over optical fiber connection.

12. The modular system of claim 10, wherein the user device is a computer or a smartphone.

13. The modular system of claim 10, further comprising one or more wireless communications adapters electrically connected to the embedded computer.

14. The modular system of claim 1, wherein the RTOS of the embedded computer is configured to run a special purpose software driver configured to transfer data from the one or more ADC modules to the embedded computer using direct memory access (DMA).

15. The modular system of claim 1, wherein the carrier board further comprises one or more battery connectors.

16. The modular system of claim 1, wherein the system is capable of being used as an electroencephalograph, an electrocardiograph, and an electromyograph.

17. A modular system for collecting and digitizing electrical signals, the system comprising:
    a carrier board comprising:
        one or more electrode connectors; and
        one or more power supplies;
        one or more analog-to-digital converter (ADC) modules, each ADC module comprising:
            multiple input channels;
            input signal routing circuitry;
            at least one instrumentation power supply;
            configuration switches for the at least one instrumentation power supply and the input signal routing;
            an ADC;
            a programmable gain amplifier; and
            an ADC communications bus, wherein
        each of the one or more ADC modules electrically connects to one of the one or more electrode connectors and one of the one or more power supplies of the carrier board;
    a field-programmable gate array (FPGA), wherein each ADC communications bus of the one or more ADC modules is directly electrically connected to the FPGA via a separate serial interface; and
    an embedded computer directly electrically connected to the FPGA via a high-speed interconnect bus.

18. The modular system of claim 17, further comprising one or more wireless communications adapters each electrically connected to the embedded computer via a serial bus.

19. The modular system of claim 17, further comprising a wired communications adapter electrically connected to the embedded computer via an electrical isolation device.

20. The modular system of claim 17, wherein the high-speed interconnect bus is an Advanced eXtensible Interface.

21. The modular system of claim 17, wherein the FPGA further includes a functional unit configured to timestamp data from each of the one or more ADC modules.

22. The modular system of claim 17, wherein the system is capable of being used as an electroencephalograph, an electrocardiograph, and an electromyograph.

23. The modular system of claim 17, wherein the carrier board further comprises one or more battery connectors.

\* \* \* \* \*